United States Patent
Fujikawa et al.

(10) Patent No.: US 8,182,454 B2
(45) Date of Patent: May 22, 2012

(54) BREAST MILK ABSORBENT PAD

(75) Inventors: Michiyo Fujikawa, Kagawa-ken (JP);
Hikari Kawakami, Kagawa-ken (JP)

(73) Assignee: Uni-Charm Corporation, Ehime (JP)

( * ) Notice: Subject to any disclaimer, the term of this patent is extended or adjusted under 35 U.S.C. 154(b) by 870 days.

(21) Appl. No.: 11/759,961

(22) Filed: Jun. 8, 2007

(65) Prior Publication Data
US 2007/0287978 A1    Dec. 13, 2007

(30) Foreign Application Priority Data
Jun. 8, 2006  (JP) .................................. 2006-160342

(51) Int. Cl.
*A61F 13/15*    (2006.01)
*A61F 13/20*    (2006.01)
(52) U.S. Cl. ................................................ 604/385.07
(58) Field of Classification Search ............. 604/385.07, 604/385.01, 385.24, 385.27
See application file for complete search history.

(56) References Cited

U.S. PATENT DOCUMENTS

| | | | |
|---|---|---|---|
| 5,690,536 A | * | 11/1997 | Madden et al. ................. 450/37 |
| 5,843,062 A | | 12/1998 | Reidmiller |
| 6,036,577 A | | 3/2000 | Coburn |

FOREIGN PATENT DOCUMENTS

| | | |
|---|---|---|
| EP | 0 544 045 A1 | 11/1991 |
| JP | 62-20407 | 5/1987 |
| JP | 1-83005 | 6/1989 |
| JP | 04-209802 | 7/1992 |
| JP | 2000-178805 | 6/2000 |
| JP | 2001-011705 | 1/2001 |

OTHER PUBLICATIONS

English translation of JP 2000-178805 A to Mikami et al.*
Extended Search Report from corresponding European application No. 07 741 705.3 issued Jan. 7, 2011, 9 pgs.

* cited by examiner

*Primary Examiner* — Melanie Hand
(74) *Attorney, Agent, or Firm* — Brinks Hofer Gilson & Lione

(57) ABSTRACT

A breast milk absorbent pad includes side flaps of a breast milk absorbent pad having first portions facing the wearer's skin and second portions facing away from the wearer's skin. The second portions are provided with elastically stretchable/contractible members along transversely opposite outer edges of these second portions.

4 Claims, 4 Drawing Sheets

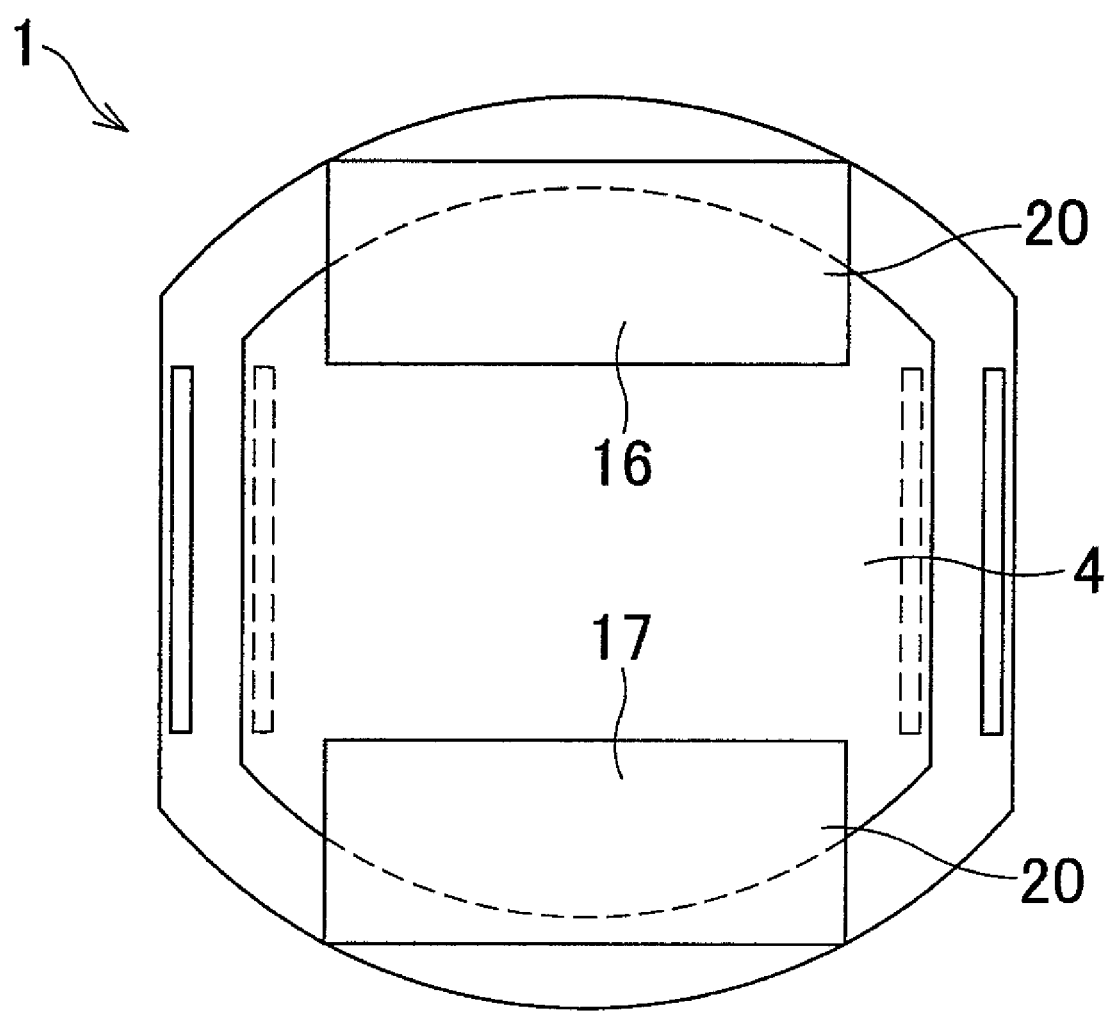

BREAST MILK ABSORBENT PAD

BACKGROUND OF THE INVENTION

The present invention relates generally to a breast milk absorbent pad adapted to be put on a wearer's skin so as to be covered with the other wearing article such as a brassiere.

Breast milk absorbent pads have conventionally been well known, which typically comprises a liquid-absorbent layer and a liquid leak-barrier sheet covering the outer surface of the liquid-absorbent layer. For example, both Japanese Unexamined Patent application Publication No. 2000-178805 (hereinafter referred to as "Reference 1") and Japanese Unexamined Patent application Publication No. 2001-11705 (hereinafter referred to as "Reference 2") disclose the breast milk absorbent pad generally comprising a pad-chassis composed of a body fluid absorbent structure and a leak-barrier sheet attached to the outer side of the absorbent structure, and a pair of elastically stretchable/contractible members respectively extending along transversely opposite edges of the absorbent structure, of which the contractile force causes the pad-chassis to be appropriately curved.

However, the breast milk absorbent pads disclosed in References 1 and 2 have left various problems behind unsolved. For example, a plurality of irregular gathers are formed along the transversely opposite edges of the breast milk absorbent pad under the contractile force of the elastically stretchable/contractible members and these gathers are directly pressed against the wearer's skin. Consequentially, these gathers may cause a feeling of discomfort for the wearer and often leave compression marks on the wearer's skin. In addition to such problems, it is likely that the transversely opposite edges of the pad might fail to be kept in close contact with the wearer's skin, resulting in leak of breast milk.

Usually, the breast milk absorbent pad may be inserted between the wearer's skin and the associated brassiere which has been spaced apart from the wearer's skin in order to wear the pad and the breast milk absorbent pad may be slipped down but not taken off in order to breast-feed a baby. In these cases, the type of breast milk absorbent pad as disclosed in References 1 and 2 may have the upper end of the pad unintentionally folded inward under the contractile force of the elastically stretchable/contractible members provided along the transversely opposite edges thereof. If it is intended to insert the breast milk absorbent pad having the upper end or the lower end folded inward between the brassiere and the wearer's skin from above or beneath, the folded upper or lower end may catch on the wearer's skin or the inner side of the brassiere and further folded inward or outward. Thus the breast milk absorbent pad as a whole may sometimes be folded inward or outward and it may be impossible to wear the breast milk absorbent pad. If it is intended to wear the breast milk absorbent pad folded in this manner, not only the wearer's skin will experience a feeling of discomfort but also an effective area for absorption will be unacceptably reduced due to the liquid-barrier material folded inward or outward with respect to the pad, possibly resulting in leak of breast milk.

In addition, if the breast milk absorbent pad fastened to the brassiere at a center thereof is slipped down in order to breast-feed her baby, the upper and lower ends of the breast milk absorbent pad already in a folded state will be further folded inward with respect to the breast milk absorbent pad under the contractile force of the elastically stretchable/contractible members. When the brassiere is repositioned after her baby has been breast-fed, the wearer must properly unfold the pad.

SUMMARY OF THE INVENTION

In view of the problem as has been described above, it is an object of the present invention to provide a breast milk absorbent pad improved so that the pad can be smoothly put on and taken off while the pad is retained in its shape curved in conformity to a shape of breast without any anxiety that upper and lower ends of the pad might be unintentionally folded inward.

The object set forth above is achieved, according to the present invention, by an improvement in a breast milk absorbent pad having a longitudinal direction and a transverse direction and comprising a pad-chassis having a first surface facing a wearer's skin and a second surface facing away from the wearer's skin, the pad-chassis being composed of a body fluid absorbent layer inclusive of a body fluid absorbent assembly and a body fluid leak-barrier sheet defining the second surface, and a pair of elastically stretchable/contractible members extending along transversely opposite sides of the pad-chassis in a longitudinal direction in order to deform the first surface in a concave shape.

The improvement according to the present invention is in that the pad-chassis includes side flaps extending outward from transversely opposite edges of the body fluid absorbent assembly, each of the side flaps comprising a first portion facing the skin and a second portion facing away from the skin and put flat together with the first portion, and the elastically stretchable/contractible members are stretched in the longitudinal direction and attached in such a stretched state to the transversely opposite outer edges of the second portion.

The present invention includes preferred embodiments as will be described below.

The elastically stretchable/contractible members comprise first elastically stretchable/contractible members attached to the first portion and second elastically stretchable/contractible members attached to the body fluid absorbent assembly along transversely opposite edges thereof.

The body fluid absorbent layer includes a body fluid pervious inner sheet covering an absorbing surface of the body fluid absorbent layer, and the first portions of the side flaps are respectively defined by portions of the inner sheet extending outward in the transverse direction from the transversely opposite edges of the body fluid absorbent assembly while the second portions of the side flaps are respectively defined by portions of the body fluid leak-barrier sheet extending outward in the transverse direction from the transversely opposite edges of the body fluid absorbent assembly.

The body fluid absorbent assembly includes a high stiffness region at least one of upper and lower end portions as viewed in the longitudinal direction and a value of stiffness in the high stiffness region is higher than that in a remaining region.

At least longitudinally opposite outer end portions of the high stiffness region extend outward beyond the longitudinally opposite ends of the elastically stretchable/contractible member in a stretched state.

In the breast milk absorbent pad according to the invention, the pad-chassis is provided with a pair of the side flaps extending laterally from the respective side edges of the body fluid absorbent assembly and each of the side flaps comprises the first portion facing the wearer's skin and the second portion facing away from the wearer's skin and put flat together with the first portion. The second portion is provided with the elastically stretchable/contractible members extending along the outer side edge thereof. Consequentially, while the second portion lying on the outer surface of the breast milk absorbent pad and facing away from the wearer's skin is formed with gathers under the contractile force of the elastically stretchable/contractible members, such contractile force of the elastically stretchable/contractible members does not directly act upon the first portion facing the wearer's skin. As a result, the first portion facing and contacting the wearer's skin is not formed with the gathers causing a feeling of discomfort for the wearer and/or leaving compression marks on the wearer's skin. At the same time, the second portion is kept in close contact with the wearer's skin and thereby reliably prevents leak of breast milk.

The preferred embodiments of the present invention provide highly important effects as will be described below.

In the embodiment of the invention wherein the body fluid absorbent assembly includes a high stiffness region at least one of upper and lower end portions, when it is intended to insert the breast milk absorbent pad between the brassiere and the wearer's skin from above or beneath, there is no anxiety that the folded upper or lower end might catch on the wearer's skin or the inner side of the brassiere so as to be unintentionally folded in- or outwardly of the breast milk absorbent pad. Therefore, the breast milk absorbent pad can be easily put inside the brassiere and comfortably worn without any likelihood that the wearer's skin might experience a feeling of discomfort due to the lower or upper end portions of the breast milk absorbent pad folded in- or outward and the effective absorbent area of the body fluid absorbent assembly might be reduced due to the body fluid leak-barrier sheet folded in- or outwardly of the breast milk absorbent pad.

In the embodiment of the invention wherein at least the outer end portion of the high stiffness region as viewed in the longitudinal direction extends outward in the longitudinal direction beyond the ends of the elastically stretchable/contractible members stretched in the longitudinal direction, the possibility that the pad-chassis might be unintentionally folded as has been described above can be further reliably avoided because at least the outer end portions of the high stiffness region are not directly influenced by the contractile force of the elastically stretchable/contractible members.

BRIEF DESCRIPTION OF THE DRAWINGS

FIG. 6 is a plan view of an alternative embodiment in which a reinforcing layer is affixed to the outer surface of the absorbent assembly.

DETAILED DESCRIPTION OF THE PREFERRED EMBODIMENTS

Details of a breast milk absorbent pad according to the present invention will be more fully understood from the description given hereunder with reference to the accompanying drawings.

Figure 1:
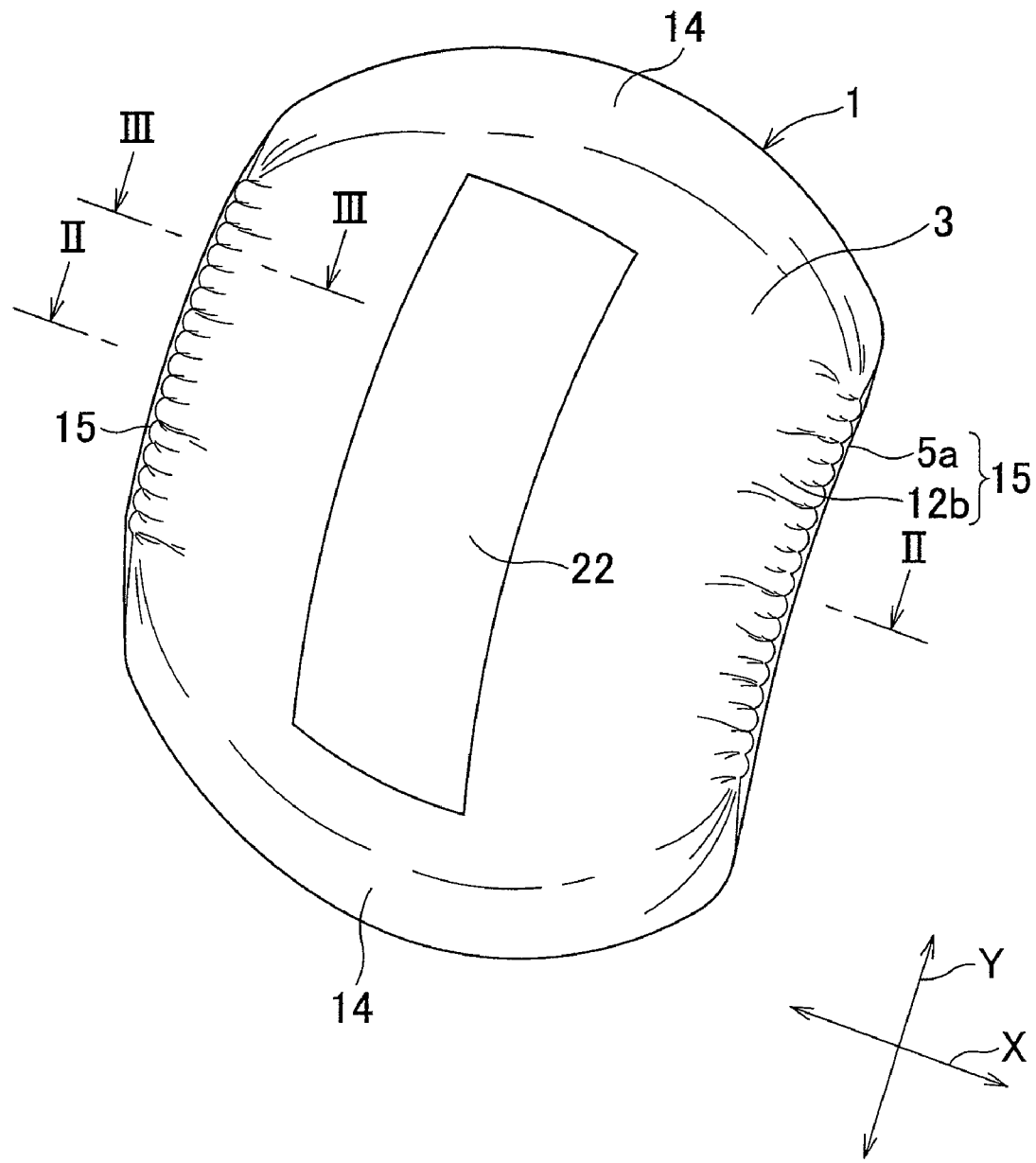
FIG. 1 is a perspective view of a breast milk absorbent pad as viewed from outside.
Figure 2:
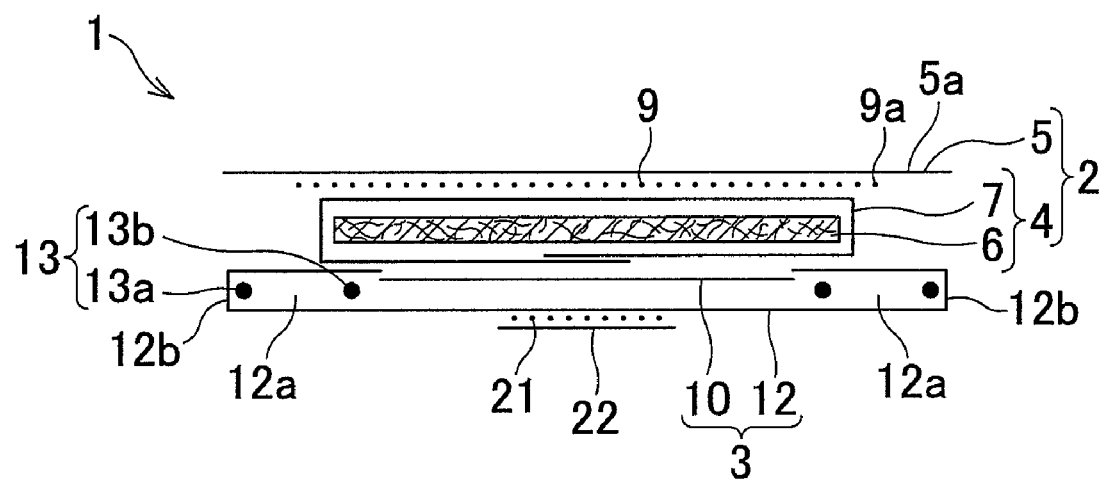
FIG. 2 is a schematic sectional view taken along the line II-II in FIG. 1.

FIG. 1 is a perspective view of a breast milk absorbent pad as viewed from the outside and FIG. 2 is a schematic sectional view taken along the line II-II in FIG. 1. As will be apparent from FIG. 1, the breast milk absorbent pad includes a pad-chassis 1 externally shaped substantially in ellipsoid having its major axis extending in a longitudinal direction of the pad. The pad-chassis 1 comprises a body fluid absorbent layer 2 and a body fluid leak-barrier sheet 3. The body fluid absorbent layer 2 comprises a body fluid absorbent assembly 4 and a body fluid-pervious inner sheet 5 covering an inner surface (corresponding to an upper surface as viewed in FIG. 2) of the body fluid absorbent assembly 4. The absorbent assembly 4 comprises a body fluid absorbent core 6 entirely wrapped with a body fluid-spreadable shape retaining sheet 7.

The core 6 is provided in the form of a panel primarily comprising fluff pulp with which super-absorbent polymer particles. This panel preferably has a basis weight in a range of 100 to 600 g/m$^2$. The shape retaining sheet 7 may be tissue paper or the like intermittently coated with hot melt adhesives (not shown) by means of which the shape retaining sheet 7 is fixed to the core 6. In this way, the shape retaining sheet 7 is kept to cover the core 6 so that the shape of the core 6 is reliably retained and materials of the core 6, particularly the polymer particles, are protected against falling off.

The inner sheet 5 facing the wearer's skin is formed preferably by a non-woven fabric made of thermoplastic synthetic fibers or a perforated film or more preferably by a non-woven fabric such as a spunbond or air-through non-woven fabric, in any case, having a basis weight in a range of 10 to 40 g/m$^2$. The inner sheet 5 is intermittently coated with hot melt adhesives 9 by means of which the inner sheet 5 is fixed to the absorbent assembly 4 so that the inner sheet 5 is maintained to cover the absorbent assembly 4. It is possible to exploit the inner sheet 5 as a multilayered structure comprising a non-woven fabric and a perforated film. Transversely opposite edges 5a (first portions) of the inner sheet 5 as well as transversely opposite edges 9a of the adhesive 9 coated region thereof extend outward beyond transversely opposite edges of the absorbent assembly 4.

The leak-barrier sheet 3 underlying the absorbent assembly 4 typically comprises a plastic film 10 preferably having a basis weight in a range of 10 to 40 g/m$^2$, a non-woven fabric 12 made of thermoplastic synthetic fibers preferably having a basis weight in a range of 10 to 40 g/m$^2$ and extending outward beyond outer peripheries of the film 10 and the absorbent assembly 4 so as to define the outer surface of the pad chassis 1 and to face the associated brassiere, and a laminated non-woven fabric preferably of spun bond/melt blown/spun bond (SMS) type. The film 10 and the non-woven fabric 12 are bonded together by means of hot melt adhesives (not shown) along transversely opposite edges of the film 10.

The outer surface of the pad-chassis 1 defined by the non-woven fabric is advantageously less slippery with respect to the associated wearing article such as a brassiere than the case in which the outer surface is defined by a plastic film and there is substantially unlikely that the breast milk absorbent pad might slip off from such wearing article. In addition, it is unnecessary to use any excessive amount of adhesives to prevent undesirable slippage of the pad and the area to be coated with adhesives as well as the amount of adhesives can be correspondingly reduced.

Transversely opposite edges of the non-woven fabric 12 are folded back inwardly of the pad-chassis 1 to form sleeves 12a. Lateral edges 12b (second portions) of the respective sleeves 12a extend outward beyond the lateral edges of the absorbent assembly 4 by substantially the same dimension as the lateral edges 5a of the inner sheet 5. In this regard, it is also possible to constitute the leak-barrier sheet from a plastic film and a thermoplastic non-woven fabric laminated on the outer surface of the plastic film so as to sandwich an elastically stretchable/contractible member 13 as will be describe later.

The pad chassis 1 includes end flaps 14 and side flaps 15 both defined by respective portions of the leak-barrier sheet 3 and the inner sheet 5 extending outward beyond the outer peripheral edge of the absorbent assembly 4 (See FIG. 1). More specifically, the side flaps 15 are respectively defined by the transversely opposite extension portions 5a of the inner sheet 5 and the transversely opposite extension portions 12b of the leak-barrier sheet 3. These extension portions 5a, 12b extend outward beyond the transversely opposite edges of the absorbent assembly 4 and are bonded together along transversely opposite edges 9a of the adhesive 9 coated regions respectively spaced inward from the outermost edges of the respective extension portions 5a, 12b. It should be noted that FIG. 2 illustrates the extension portions 5a, 12b before bonded along the transversely opposite edges 9a of the adhesive 9 coated regions.

Figure 3:
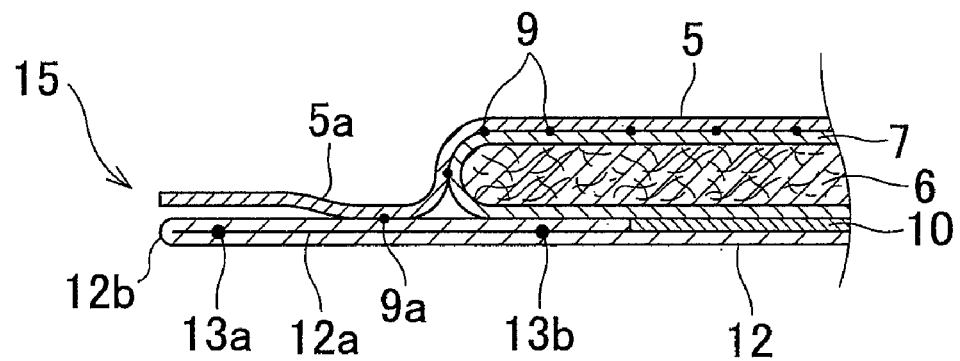
FIG. 3 is a sectional view taken along the line III-III in FIG. 1.

FIG. 3 is a sectional view taken along the line III-III in FIG. 1.

The elastically stretchable/contractible members 13 comprises first and second elastically stretchable/contractible members 13a, 13b and are elastically stretchable/contractible in a longitudinal direction Y. The first and second elastically stretchable/contractible members 13a, 13b are laid within the sleeves 12a of the leak-barrier sheet 3. Specifically, the first elastically stretchable/contractible members 13a extend along the transversely opposite edges of the respective sleeves 12a in the longitudinal direction Y while the second elastically stretchable/contractible members 13b underlie the transversely opposite edges of the absorbent assembly 4 spaced apart inward from the first elastically stretchable/contractible members 13a in a parallel relationship and extend along the edges of the absorbent assembly 4 in the longitudinal direction Y. These elastically stretchable/contractible members are respectively bonded, while they are stretched in the longitudinal direction Y, to the sleeves 12a by means of hot melt adhesives (not shown). A contractile force of the first elastically stretchable/contractible members 13a deforms the side flaps 15 so as to come in close contact with the wearer's skin while a contractile force of the second stretchable/contractible members 13b deforms the flat panel-like semirigid absorbent assembly 4 having a rigidity higher than those of the leak-barrier sheet 3 as well as the inner sheet 5 both having a high flexibility so that the absorbent assembly 4 inclusive of these sheets 3, 5, i.e., the pad-chassis 1 as a whole may be concavely curved with the inner sheet 5 inside, in other words, convexly curved with the leak-barrier sheet 3 outside.

These elastically stretchable/contractible members are fixed to the leak-barrier sheet along the transversely opposite edges thereof in this manner and therefore the transversely opposite edges 5a (first portions) of the inner sheet coming in close contact with the wearer's skin are free from being directly affected by a tensile stress of the elastically stretchable/contractible members. Consequentially, there is no anxiety that the transversely opposite edges 5a of the inner sheet might be formed with undesirable gathers which would cause the wearer to experience a feeling of discomfort and/or leave compression marks on the wearer's skin. Thus the transversely opposite edges 5a of the inner sheet are reliably held in close contact with the wearer's skin and thereby leak of breast milk can be effectively prevented.

The elastically stretchable/contractible member 13 is made of natural or synthetic rubber and preferably has a tensile force in a range of 115 to 500 mN.

A stretching ratio and a tensile force of the elastically stretchable/contractible member 13 are measured by a method described below.

A portion (referred to hereinafter as "effective length") of the elastically stretchable/contractible member 13 fixed in a stretched state having a length of 40 mm is cut away from the pad-chassis and adhesives clinging to the elastically stretchable/contractible member 13 is removed to obtain a specimen of the elastically stretchable/contractible member. The stretching ratio of the elastically stretchable/contractible member is obtained according to an equation of stretching ratio=40/W wherein W (mm) is a measured length of this specimen of the elastically stretchable/contractible member. The tensile force of the elastically stretchable/contractible member 13 is measured utilizing 5540 Series Single Column Tester System manufactured by INSTRON. Specifically, the specimen of the elastically stretchable/contractible member 13 is held by chucks spaced from each other by a distance of 30 mm, then stretched at a rate of 100 mm/min and the tensile force at the stretching ratio measured by said method is determined.

If the effective length is less than 40 mm, the length (W mm) of the elastically stretchable/contractible member 13 having such effective length cut away may be measured. In this case, the stretching ratio may be calculated according to the equation of stretching ratio=effective length/W and the tensile force may be measured by the method as has been described just above with the distance between the chucks set to the effective length minus 10 mm.

Figure 4:
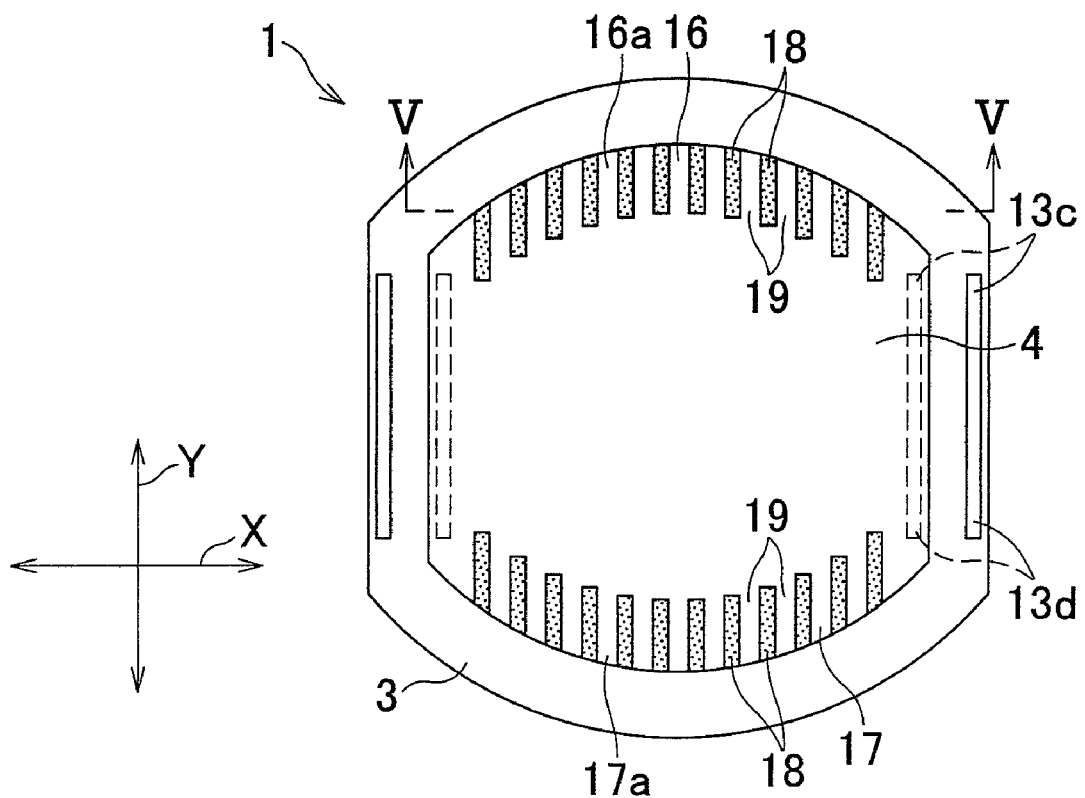
FIG. 4 is a plan view showing the absorbent assembly having an embossed region.
Figure 5:
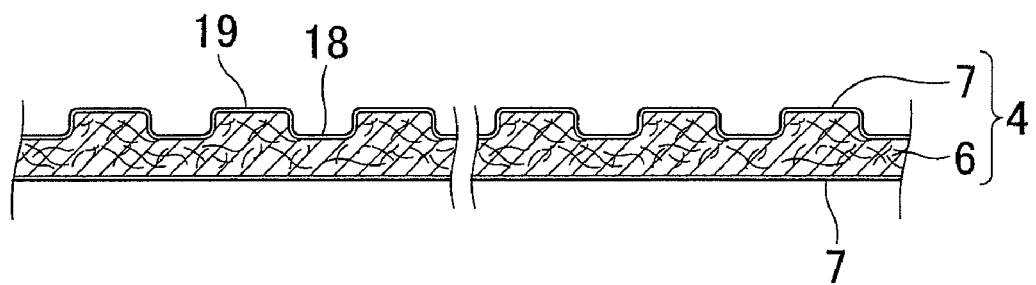
FIG. 5 is a sectional view taken along the line V-V in FIG. 4.

FIG. 4 is a plan view of the pad-chassis 1 having the inner sheet 5 removed and the sleeves 12a not shown and FIG. 5 is a sectional view taken along the line IV-IV in FIG. 3. The absorbent assembly 4 is provided along upper and lower ends thereof with embossed high stiffness regions 16, 17, respectively. The embossed regions 16, 17 have a higher stiffness in comparison to the remaining region. The high stiffness regions 16, 17 respectively comprise a plurality of embossed lines (i.e., compressed grooves) 18 and ridges 19 defined between each pair of the adjacent compressed grooves 18 both extending in the longitudinal direction Y so as to define together a surface repetitively patterned indented in the transverse direction X as will be apparent from FIG. 5. The absorbent assembly 4 is shaped substantially in ellipsoid and has the high stiffness regions 16, 17 describing circular arcs which are convex upward and downward, respectively. The leak-barrier sheet 3 and the inner sheet 5 (not shown) are also shaped substantially in ellipsoid so that the pad-chassis 1 is also shaped substantially in ellipsoid in its flat panel-like state free from a bowing effect of the elastically stretchable/contractible member 13. In the high stiffness regions 16, 17, the ridges 19 also are more or less compressed as the compressed grooves 18 are formed and consequentially these high stiffness regions 16, 17 as a whole have a thickness smaller than in the remaining region.

Specifically, the pad-chassis 1 has a thickness in a range of 3.0 mm to 3.8 mm in the embossed regions and a thickness in a range of 4.0 mm to 4.8 mm in the remaining region. The pad-chassis 1 constructed in the manner as has been described above can be smoothly inserted between the associated brassiere and the wearer's skin without a trouble that the upper end and/or the lower end of the pad-chassis 1 might be folded back.

At least the outermost ends 16a, 17a of the high stiffness regions 16, 17 as viewed in the longitudinal direction Y preferably extend outward beyond respective ends 13c, 13d of the elastically stretchable/contractible member 13. This is for the reason that the contractile force of the elastically stretchable/ contractible member 13 will not directly act upon the respective outermost ends 13c, 13d extending outward beyond the respective ends 13c, 13d and therefore the upper and lower ends of the pad-chassis 1 can be further reliably prevented from being folded back. Although not shown, it is possible to emboss the absorbent assembly 4 together with the inner sheet 5 with which the absorbent assembly 4 is covered.

FIG. 6 illustrates a manner in which a reinforcing layer 20 comprising a separately provided high basis weight non-woven fabric or an embossed non-woven fabric has been attached to each of the upper and lower ends of the absorbent assembly 4 instead of embossing the absorbent assembly 4. The reinforcing layer 20 is not limited to the above-mentioned non-woven fabric but may be formed by from layer of urethane foam or silicon or even by a layer of hot melt adhesives coated on the absorbent assembly 4.

The high stiffness regions 16, 17 have a flexural stiffness preferably in a range of 0.5 to 2.0 N·cm, more preferably in a range of 0.8 to 1.5N·cm. The flexural stiffness of the embossed regions (i.e., high stiffness regions) is preferably in a range of 0.8 N·cm to 1.5 N·cm. So far as the flexural stiffness of the embossed regions is in such a range, there is no anxiety that the high stiffness regions as well as the upper and lower ends extending in the vicinity of these regions might be folded inward. If the flexural stiffness of the embossed regions is 0.8 N·cm or less, there is a possibility that the high stiffness regions as well as the upper and lower ends extending in the vicinity of these regions might be folded inward and if the flexural stiffness of the embossed regions is 1.5 N·cm or more, the excessively high stiffness may cause the wearer's skin to experience a feeling of discomfort.

While not illustrated, it is preferred to interpose a compression reversing elastic layer comprising hydrophilic and/or hydrophobic fibers between the absorbent assembly 4 and the inner sheet 5 in order to alleviate the stiffness of the pad-chassis 1 containing the absorbent assembly 4 and to give the wearer a soft feeling to wear the breast milk absorbent pad.

Referring again to FIG. 1, the leak-barrier sheet 3 is coated on the outer surface thereof with a pressure-sensitive adhesive layer 21 by means of which the breast milk absorbent pad is affixed to the associated wearing article such as the brassiere and this pressure-sensitive adhesive layer 21 is covered with a separator 22.

The present invention can provide a breast milk absorbent pad improved so that the pad can be smoothly put on and taken off while the pad is retained in its shape curved in conformity to a shape of breast without any anxiety that upper and lower ends of the pad might be unintentionally folded inward.

The entire discloses of Japanese Patent application No. 2006-160342 filed on Jun. 8, 2006 including specification, drawings and abstract are herein incorporated by reference in its entirety.

What is claimed is:

1. A breast milk absorbent pad having a longitudinal direction and a transverse direction and comprising:
    a pad-chassis having a first surface facing a wearer's skin and a second surface facing away from the wearer's skin;
    said pad-chassis being composed of a body fluid absorbent layer inclusive of a body fluid absorbent assembly and a body fluid leak-barrier sheet defining said second surface, and a pair of elastically stretchable/contractible members extending along transversely opposite sides of said pad-chassis in a longitudinal direction in order to deform said first surface in a concave shape;
    said pad-chassis including side flaps extending outward from transversely opposite edges of said body fluid absorbent assembly, each of said side flaps comprising a first portion facing said skin and a second portion facing away from said skin and put flat together with said first portion;
    said elastically stretchable/contractible members being stretched in said longitudinal direction and attached in such a stretched state to the transversely opposite outer edges of each of said second portions, exclusively with respect to the first portions; and
    said body fluid absorbent assembly having longitudinally opposed upper and lower sides and further including a high stiffness region located exclusively so as to contact and extend inward from a peripheral edge of the body fluid absorbent assembly at least one of the upper and lower sides without extending longitudinally across a major portion of the distance between said upper and lower sides of the body fluid absorbent assembly, and a value of stiffness in said high stiffness region being higher than that in a remaining region of said body fluid absorbent assembly, wherein said high stiffness region comprises a plurality of compressed grooves and ridges defined between each pair of adjacent ones of said compressed grooves both extending in the longitudinal direction so as to define together a surface that is repetitively patterned in an indented manner in the transverse direction.

2. The breast milk absorbent pad as defined by claim 1, wherein said elastically stretchable/contractible members comprise first elastically stretchable/contractible members attached to said first portion and second elastically stretchable/contractible members attached to said body fluid absorbent assembly along transversely opposite edges thereof.

3. The breast milk absorbent pad as defined by claim 1, wherein said body fluid absorbent layer includes a body fluid pervious inner sheet covering an absorbing surface of said body fluid absorbent layer and wherein said first portions of said side flaps are respectively defined by portions of said inner sheet extending outward in said transverse direction from the transversely opposite edges of said body fluid absorbent assembly while said second portions of said side flaps are respectively defined by portions of said body fluid leak-barrier sheet extending outward in said transverse direction from the transversely opposite edges of said body fluid absorbent assembly.

4. The breast milk absorbent pad as defined by claim 1, wherein at least the outer end portion of said high stiffness region as viewed in said longitudinal direction extends outward in said longitudinal direction beyond the ends of said elastically stretchable/contractible members stretched in said longitudinal direction.

* * * * *